United States Patent [19]

Ruhe

[11] Patent Number: 4,897,390

[45] Date of Patent: Jan. 30, 1990

[54] NOVEL ANTI-OBESITY COMPOUNDS AND METHOD OF USE

[76] Inventor: Rodney C. Ruhe, 1000 Willmar Ave., SW., Willmar, Minn. 56201

[21] Appl. No.: 76,077

[22] Filed: Jul. 21, 1987

[51] Int. Cl.$^4$ .............................................. A61K 31/56
[52] U.S. Cl. .................................... 514/177; 514/909
[58] Field of Search ...................... 260/397.4; 514/909, 514/177

[56] References Cited

U.S. PATENT DOCUMENTS

| | | |
|---|---|---|
| 4,137,327 | 1/1979 | Marshall . |
| 4,379,842 | 4/1983 | Fujiwara et al. . |
| 4,518,595 | 5/1985 | Coleman et al. . |
| 4,602,008 | 7/1986 | Kresk . |
| 4,657,759 | 4/1987 | Hansen et al. . |

FOREIGN PATENT DOCUMENTS 0133995 2/1984 European Pat. Off. .

OTHER PUBLICATIONS

Kappas, A., Hellman, L., Fukushima, K., Gallagher, T. F., "The Thermogenic Effect and Metabolic Fate of Etiocholanone in Man," 18, J. Endocrin. & Metab. Oct., 1958, pp. 1043–1055.
Coleman, D. L., Leiter, E. H., Schwizer, R. W., "Therapeutic Effects of Dehydroepiandrosterone (DHEA) in Diabetic Mice", 31, Diabetes Sep. 1982, pp. 830–833.
Schwartz, A. G., Hard, G. C., Pashko, L. L., Abou-Gharbia, M., "Dehydroepiandrosterone: An Anti-Obesity and Anti-Carcinogenic Agent", 3, Nutrition and Cancer, 1983, pp. 46–52.
Yen, T. T., Allan, J. A., Pearson, D. V., Acton, J. M., Greenberg, M. M., "Prevention of Obesity in A$^{vy}$/a Mice by Dehydroepiandrosterone," 12, Lipids, pp. 409–413.
Coleman, D. L., Leiter, E. H., Applezweig, N., "Therapeutic Effects of Dehydroepiandrosterone Metabolites in Diabetes Mutant Mice (C57BL/KsJ-db/db)," 115, Endocrinology, 1984, pp. 239–243.
Pashko, L. L., Hard, G. C., Rovito, R. J., Williams, J. R., Sobel, E. L. & Schwartz, A. G., "Inhibition of 7,12-dimethylbenz(a)anthracene-induced Skin Papillomas & Carcinomas by Dehydroepiandrosterone 3-beta-methyl-androst-5-en-17-one in Mice," 45, Cancer Res., pp. 164–166.
J. Am. Chem. Soc. 80: 1769–1770 (1958), Mueller G. P. et al.
Abou-Gharbia, M.; et al., J. of Pharm. Sc., vol. 70, No. 10, Oct. 87, 1154–1157 (1981).
Mueller, G., W. F. Johns, J. Org. Chem. 26: 2403–2412 (1961).

Primary Examiner—H. M. S. Sneed
Assistant Examiner—James Saba
Attorney, Agent, or Firm—Limbach, Limbach & Sutton

[57] ABSTRACT

The present invention provides novel compounds for controlling mammalian obesity by simultaneous action upon caloric intake and caloric expenditure. This is accomplished by the administration of pharmaceutically acceptable and therapeutically active analogs of α-HET and β-HET, having a methyl group at the 3β position to avoid metabolically induced conjugation of the molecule to an inactive species while retaining the structural integrity of the molecule.

20 Claims, 3 Drawing Sheets

BODY WEIGHT OF CONTROL AND β-MET-TREATED MALE (TOP PANEL),
AND CONTROL AND β-MET- TREATED FEMALE (BOTTOM PANEL) C57-WH MICE.
CURVES ILLUSTRATE MEAN BODY WEIGHT ± S.E.

BODY WEIGHT OF CONTROL AND β-MET-TREATED MALE (TOP PANEL),
AND CONTROL AND β-MET- TREATED FEMALE (BOTTOM PANEL) C57-WH MICE.
CURVES ILLUSTRATE MEAN BODY WEIGHT ± S.E.

FIG. 6

CUMULATIVE FOOD CONSUMPTION OF CONTROL AND β-MET-TREATED MALE AND OF CONTROL AND β-MET-TREATED FEMALE C57-WH MICE AFTER 14 WEEKS OF TREATMENT.

NOVEL ANTI-OBESITY COMPOUNDS AND METHOD OF USE

TECHNICAL FIELD

This invention relates generally to the use of steroid compounds in the reduction of mammalian obesity. In particular, this invention relates to the synthesis and use of etiocholanone derivatives as anti-obesity agents.

BACKGROUND OF THE INVENTION

Weight reduction is accomplished when the body takes in fewer calories than it expends. Thus, all weight control measures involve strategies for either reducing caloric intake, or, increasing energy expenditure. For example, diets achieve weight reduction by directing an individual to consume food sufficient to maintain nutritional balance but insufficient to maintain body weight. U.S. Pat. No. 4,137,327 to Marshall claims an analogous process whereby a mixture of albumin and oxethazine is swallowed prior to eating. The mixture purportedly clings to the walls of the stomach and anesthetizes the nerve endings which activate digestive fluids. The process thereby permits eating without caloric intake. On the other hand, exercise or activity programs achieve weight reduction by increasing the body's rate of caloric expenditure. Such programs are effective when they specify normal levels of food consumption and greater than normal levels of exercise.

It follows that the most efficient weight reduction strategy would simultaneously decrease caloric intake while increasing caloric expenditure. To this end, dehydroepiandrosterone ("DHEA") is a promising anti-obesity agent. The exact mechanism by which DHEA effects weight loss is not known. However, experimental evidence suggests that DHEA inhibits particular metabolic enzymes (and thus caloric intake) while simultaneously increasing the overall metabolic rate (and therefor caloric expenditure).

For instance, as to its inhibitory effect, DHEA is known to inhibit mammalian glucose-6-phosphate dehydrogenase ("G6PD"). Marks, P. A. and J. Banks. 1960. *Inhibition of glucose-6-phosphate dehydrogenase by steroids.* PNAS USA 16:447–452; Oertel, G. W. and P. Benes. 1972. *The effect of steroids on glucose-6-phosphate dehydrogenase.* J. Steroid Biochem. 3:493–496; Lane, M. D. and J. Moss. 1971, in Vogel, H. J. (ed) *Metabolic Pathways.* Vol. 5. Academic Press. New York. Pg. 23. G6PD is the first enzyme in the pentosephosphate shunt, a primary source of extra-mitochondrial NADPH required for the biosynthesis of fatty acids and nucleic acids. The results of DHEA treatment in mice, where decreases in lipogenesis and fat cell size were found, suggest a primary effect on lipogenesis in vivo. Yen, T. T., J. A. Allan, D. V. Pearson, J. M. Acton and M. M. Greenberg. 1977. *Prevention of obesity in A<sup>vy</sup>/a mice by dehydroepiandrosterone.* Lipids 12:409–413; Cleary, M. P., R. Seidenstat, R. H. Tannen, and A. G. Schwartz, 1982. *The effect of dehydroepiandrosterone on adipose tissue cellularity in mice.* Proc. Soc. Exp. Biol. Med. 171:276.

DHEA is also a known inhibitor of NADH oxidase, the first enzyme of the cytochrome system. Crane, F. L., Y. Hatefi, R. L. Lester, and C. Widmer. 1957. *Isolation of a quinone from beef heart mitochondria.* Biochim. Biophys. Acta. 25:220–221. Cytochrome is an indispensable component of mitochondrial oxidative phosphorylation, the principal source of ATP required for the biosynthesis of fatty acids. Thus, by limiting the availability of mitochondrial ATP, DHEA may inhibit the process of fat deposition.

In addition, DHEA is known to directly inhibit fatty acid synthetase. Spydevold, B. O., A. L. Greenbaum, N. Z. Baguer, and P. McLean, 1978, *Adaptive responses of enzymes of carbohydrate and lipid metabolism to dietary alteration in genetically obese Zucker rats (fa/fa),* Eur. J. Biochem., 89:329–339; Michaelis, O. E., D. J. Scholfield, L. B. Gardner, and S. Cataland. 1980. *Metabolic responses of Zucker fatty and lean rats fed carbohydrate diets ad libitum or in meals,* J. Nutr. 110:1409–1420. Prolonged treatment with DHEA is known to decrease liver and adipose tissue fatty acid synthetase activity in mice characterized by excessive levels of this enzyme. Shepherd, A. and M. P. Cleary, 1984. *Metabolic alterations after dehydroepiandrosterone treatment in Zucker rats.* Am. J. Physiol. 246:E123–E128.

Finally, DHEA is known to inhibit $11\beta$-hydroxylase, an enzyme complex that converts 11-deoxycorticosterone to aldosterone and 11-deoxycortisol to cortisol. Sharma, D. C., E. Forchielli, and R. I. Dorfman. 1963. *Inhibition of enzymatic $11\beta$-hydroxylation by androgens.* J. Biol. Chem. 238:572–575. Since hypercorticism is a prominent feature of genetically obese mice, occurring after the onset of obesity, DHEA could limit the production of glucocorticoids and restore a more normal hormonal balance, thereby decreasing the severity of obesity.

In connection with its metabolic rate effects, DHEA is known to increase levels of thyroid stimulating hormone and thyroxine in the blood. Tal, B. and F. G. Sulman. 1973. *Dehydroepiandrosterone-induced thyrotropin release in immature rats.* J. Endocrinol. 57:183–184; Tal, B. and F. G. Sulman. 1975. *Dehydroepiandrosterone-induced thyrotropn release during heat stress in rats.* J. Endrocinol. 67:99–103. In rat studies, such increases are accompanied by hypertrophy of the thyroid follicle epithelium, suggesting that the anti-obesity effect of DHEA may also be the result of an increase in metabolic rate. Id.; Tagliaferro, A. R. and J. R. Davis. 1983. *The effective of dehyroepiandrosterone on caloric intake, body weight and resting metabolism.* Fed. Proc. 42:326.

It is hypothesized that the anti-obesity effects of DHEA are accomplished by its metabolic by-products, principally $\alpha$-hydroxy-etiocholanone ($5$-$\beta$-androstan-$3$-$\beta$-ol-$17$-one, hereinafter "$\alpha$-HET"), and, $\beta$-hydroxy-etiocholanone ($5$-$\beta$-androstan-$3$-$\beta$-ol-$17$-one, hereinafter "$\beta$-HET"). Coleman, Leiter and Applezweig, *Therapeutic Effects of Dehydroepiandrosterone Metabolites in Diabetes Mutant Mice,* Endocrinology, 115(1), 239. The conversion of DHEA to $\alpha$-HET and $\beta$-HET sometimes occurs intracellularly, where these products then exert effects on the biochemical machinery of individual cells.

The compounds and methods disclosed in the prior art serve as background for the design of anti-obesity DHEA compounds. For one, although DHEA itself exhibits relatively low toxicity in humans, the anti-obesity effects cannot be accomplished by administration of large doses. Indeed, DHEA can also be metabolized to estrogens, a process known to stimulate uterine growth in the sexually immature rat. Knudsen, T. T. and V. B. Mahesh, 1975, *Initiation of precocious sexual maturation in the immature rat treated with dehydroepiandrosterone,* Endocrinol 97:458–468. Estrogenic and androgenic effects of long-term DHEA administration have also been observed in humans. Drucker, W. D., J. M. Blumbert, and R. David. 1966. Clin. Res. 14:279. These effects clearly limit the usefulness of DHEA as an anti-obesity agent in humans.

As a second matter, the conversion of DHEA to α-HET and β-HET is sometimes accomplished intracellularly, where these products exert their biochemical effects. However, once excreted from cells to the general circulation, both α-HET and β-HET are rapidly deactivated and excreted from the body. Kappas, Hillman, Fukushima, and Gallagher, *The Thermogenic Effect and Metabolic Fate of Etiocholanone in Man*, J. Clin. Endocrin. & Metab., 18(10), 1043. Therefore, it is apparent that gross administration of DHEA metabolites is also of limited usefulness in the treatment of obesity in humans.

The common thread to the estrogenicity and steroid de-activation problems is the presence of the hydroxyl group at the 3β position of the steroid. It is known that the 3β-hydroxyl group plays a major role in directing the conversion of DHEA to estrogens and androgens. Baulieu, E. E. and F. Dray, 1963, *Conversion of $^3$H-dehydroepiandrosterone sulfate to $^3$H-estrogens in normal pregnant women*, J. Clin. Endocrinol. Metab 23:1298; MacDonald, P. C., A. Chapdelaine, O. Gonzalez, E. Gurpide, R. L. Vande Wiele, and S. Lieberman. 1965. J. Clin. Endocrinol. Metab. 25:1557; Slaunwhite, W. R., M. J. Burgett, and A. A. Sandberg. 1967. J. Clin. Endocrinol. Metab. 27:663. It is also known that de-activation of β-HET occurs by conjugation at the 3β position to glucuronic acid. The present invention provides for the replacement of the hydroxyl group with a methyl group to preclude conjugation of the molecule to glucuronic acid.

Prior designs provide no information in connection with anti-obesity properties of a 3β-MET derivative. U.S. Pat. No. 4,451,460 to Hansen et al. claims various methods for releasing human steroid mixtures into the air so as to repel deer, elk, moose, hare and similar animals. U.S. Pat. No. 4,657,759 to Hansen, et al. describes a matrix of thermoplastic polymer and human steroids for this use. U.S. Pat. No. 4,496,556 to Orentreich claims DHEA and its therapeutically effective derivatives for use in the treatment of dry skin. U.S. Pat. No. 4,542,129 to Orentreich describes the identical use of DHEA in conjunction with keratolytic agents to prevent the formation of acne-like skin lesions. U.S. Pat. No. 4,518,595 to Coleman, et al., describes the use of DHEA, its sulfated derivative and soluble DHEA compounds for enhancing pancreatic β-cell function for the treatment of diabetes. U.S. Pat. No. 4,628,052 to Peat claims the use of DHEA and DHEA derivatives in the treatment of arthritis and joint pain. Finally, while U.S. Pat. No. 4,602,008 to Krsek describes etiocholanone derivatives useful as anti-diabetic, anti-obesity and anti-erythropoietic agents, only 16-alkylated and 16-alkylated-7-hydroxy derivatives and the esters and ethers thereof are claimed.

Therefore, an object of this invention is to provide a new method of weight reduction consisting of a steroid compound which simultaneously depresses anabolic enzymes (caloric intake) and increases metabolic rate (caloric expenditure).

It is a further object of this invention to provide a new steroid composition that duplicates the anti-obesity properties of DHEA metabolites but eliminates their inherent clinical disadvantages.

More specifically, it is another object of this invention to provide an α-methyl derivative (α-MET) of α-hydroxyetiocholanone. It is a further object of this invention to provide a β-methyl derivative (β-MET) of β-hydroxyetiocholanone, the DHEA metabolite associated with anti-obesity activity.

It is a still further object of this invention to provide methods for administering α-MET and β-MET in various pharmaceutically acceptable, therapeutically effective ways.

SUMMARY OF THE INVENTION

The present invention provides 3α-methyletiocholanone ("α-MET") and 3β-methyl-etiocholanone ("β-MET"), and biologically similar, active analogs. This invention further provides methods using α-MET and β-MET to reduce and control obesity by virtue of their simultaneous action on anabolic enzymes and metabolic rate.

DETAILED DESCRIPTION OF THE INVENTION

Figures 1, 2:
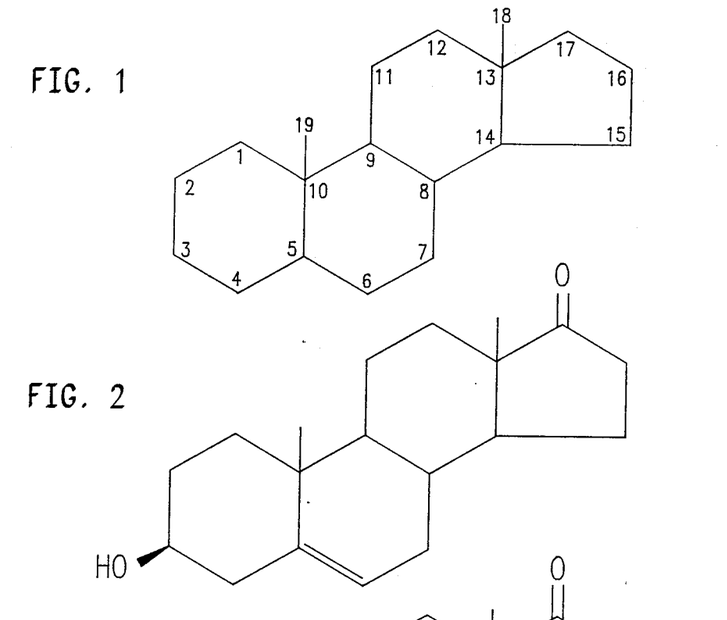
FIG. 1 is a depiction of the chemical structure of a saturated tetracyclic hydrocarbon, perhydrocyclopentanophenanthrene.
FIG. 2 is a depiction of the chemical structure of the steroid compound dehydroepiandrosterone (DHEA).

Steroids are an enormously important and diverse class of biomolecules. All members of the class are derivatives of the saturated tetracyclic hydrocarbon perhydrocyclopentanophenanthrene (FIG. 1). Steroids vary in the nature and the location of functional groups attached to the perhydrocyclopentanophenanthrene skeleton. It is well known that such chemical variations upon the basic structure accounts for the tremendous bioactive diversity among steroid compounds.

DHEA is a steroid compound characterized by an hydroxyl group at the 3β position, a ketone function at the C17 position, and a double bond between C5 and C6 (FIG. 2). DHEA is metabolized intracellularly to four isomeric products: androsterone, epiandrosterone, 3α-hydroxyetiocholanone ("α-HET"), and 3β-hydroxyetiocholanone ("β-HET"). The α-HET and β-HET metabolites are known to accomplish the anti-obesity effects attributed to DHEA, although it is not known whether DHEA effects are mediated by its metabolites in vivo. When excreted by individual cells to the blood stream, the α-HET and β-HET compounds are conjugated to glucuronic acid at the 3-hydroxy position. In addition to lacking any anti-obesity properties, the glucuronic end-product is immediately excreted from the body.

The α-HET and β-HET compounds are therefore limited in their clinical anti-obesity use by the sensitivity of the molecule to conjugation at the 3-hydroxy position. This invention relates to the preparation of analogs of α-HET and β-HET which retain the anti-obesity properties but exhibit resistance to deactivation.

In the instant invention, compounds are provided in which the 3-β-hydroxy group is replaced by a methyl group. The presence of the methyl group prevents conjugation and the consequent loss of biological activity and rapid elimination of the molecule. At the same time, the methyl group of the instant invention maintains the structural integrity and thus, the effectiveness, of the molecule. In various mammalian systems, it has been demonstrated that 3β-methyletiocholanone is a safe and effective antiobesity agent. In comparison to 3β-HET, 3β-MET is a much more effective inhibitor of obesity. The increased efficacy of 3β-MET is apparently due to the substitution of the 3-hydroxy group with a methyl group.

The compositions of the instant invention are selected from the group of α-HET and β-HET analogs having a 3β methyl group which are metabolically stable, pharmaceutically acceptable and therapeutically effective. The compositions have the following general formula:

wherein $R_1$ is selected from the group consisting of F, Cl, Br or H.

It will be understood by those of ordinary skill in the art that there are two configurations for each of the above-described analogs. There will be those α-analogs which are derived from α-HET. There will also be β-analogs which are derived from β-HET. Both classes of compounds are intended to be within the scope of the present invention.

Figures 3, 4:
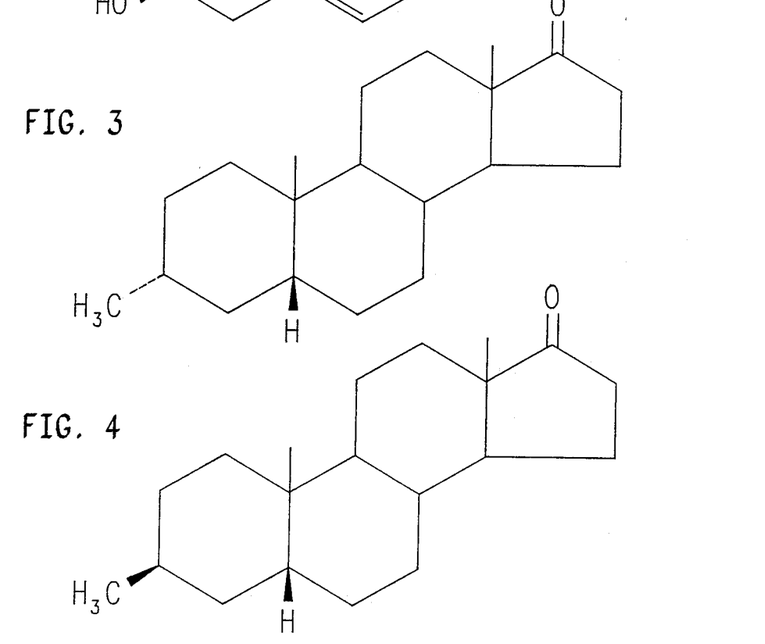
FIG. 3 is a depiction of the chemical structure of one of the steroid compound of the instant invention, 3-α-methyl-5-β-androstan-17-one (3-α-methyl-etiocholanone, α-MET).
FIG. 4 is a depiction of the chemical structure of another of the steroid compound of the instant invention, 3-β-methyl-etiocholanone, β-MET).

A particularly preferred compound of the present invention, 3-α-methyl-5-β-androstan-17-one, is shown in FIG. 3.

EXAMPLE 1

3-α-methyl-5-β-androstan-17-one was synthesized by the addition of catechol phosphochloridate (35 g, 200 mmol) and pyridine (15 g, 189.6 mmol) to 3-α-hydroxy-5-β-androstan-17-one (50.1 g, 173.0 mmol) in 1000 ml of methylene dichloride. The solution was magnetically stirred for 0.5 hour at room temperature (25° C.). Iodine (70 g, 275 mmol) was then added slowly to the solution and the stirring continued for an additional 2 hours at 25° C. The solution was washed with aqueous sodium sulfite (5%), dilute HCl, water, and dried over magnesium sulfate. It is important that the sodium sulfite solution not be saturated to prevent formation of emulsions. Approximately half of the aqueous solvent was removed under reduced pressure. Ether (2000 ml) was then added, and the entire solution passed through a short column of neutral alumina to remove colored impurities. The ether/solvent was evaporated from the column effluent under reduced pressure to yield 3α-iodo-5β-androstan-17-one. This product was pure enough to be used in the next step without recrystallization.

The 3α-iodo-5β-androstan-17-one (118.6 g, 297.0 mmol) was mixed with ethylene glycol (200 ml) and p-toluene sulfonic acid (2.0 g) in benzene (2500 ml). The mixture was refluxed under a Dean-Stark trap for 72 hours. The solution was then washed with saturated sodium bicarbonate and water, and dried over magnesium sulfate. The solvent was removed under reduced pressure and the remaining material recrystallized from ether to yield 128.7 g (98%) of 3β-iodo-5β-androstan-17-ethyleneketal.

Cuprous cyanide (20.0 g, 223.3 mmol) was placed in a dry 500 ml 3-neck round bottom flask equipped with a magnetic stirrer. The system was flushed with nitrogen and dry tetrahydrofuran (100 ml) was added to the flask. The suspension was cooled to $-70°$ C. and methyllithium 1.5M (in diethyl ether, 290 ml, 436 mmol) was added via cannula. The solution was allowed to warm to 0° C. for 5 minutes, which resulted in a clear tan solution. After recooling to $-70°$ C., the 3β-iodo-5β-androstan-17-ethyleneketal (24.2 g, 54.5 mmol) in 100 ml dry tetrahydrofuran was added via a syringe. The solution was then warmed to room temperature (25° C.) and stirred for 18 hours under nitrogen. The solution was extracted with 250 ml of 90% saturated $NH_4Cl$/10% conc. $NH_4OH$. The solvent was removed under reduced pressure. Recrystallization from methanol (600 ml) yielded 3α-methyl-5β-androstan-17-ethyleneketal, 14.09 g (78%).

The 3α-methyl-5β-androstan-17-ethyleneketal (11.20 g, 33.8 mmol) was dissolved in acetone (250 ml). p-Toluene sulfonic acid (200 mg) and $H_2O$ (80 ml) were added and the solution refluxed for 2 hours. The solution was evaporated, taken up in ether (80 ml), washed with saturated sodium bicarbonate and water, then dried over magnesium sulfate. The solution was filtered and evaporated to give a colorless solid which was recrystallized from methanol to yield 3α-methyl-5β-androstan-17-one as colorless plates (8.74 g, 90%). The melting point of this composition is 141°–143° C.

Another particularly preferred compound of the instant invention, 3-β-methyl-5-β-androstan-17-one, is depicted in FIG. 4.

EXAMPLE 2

3-β-methyl-5-β-androstan-17-one was synthesized by the addition of catechol phosphochloridate (35 g, 200 mmol) and pyridine (15 g, 189.6 mmol) to 3-β-hydroxy-5-β-androstan-17-one (50.1 g, 173.0 mmol) in 1000 ml of methylene dichloride. The solution was magnetically stirred for 0.5 hour at room temperature (25° C). Iodine (70 g, 275 mmol) was then added slowly to the solution and the stirring continued for an additional 2 hours at 25° C. The solution was washed with aqueous sodium sulfite (5%), dilute HCl, water, and dried over magnesium sulfate. It is important that the sodium sulfite solution not be saturated to prevent formation of impulsions. Approximately half of the aqueous solvent was removed under reduced pressure. Ether (2000 ml) was then added, and the entire solution passed through a short column of neutral alumina to remove colored impurities. The ether/solvent was evaporated from the column effluent under reduced pressure to yield 3β-iodo-5β-androstan-17-one. This product was pure enough to be used in the next step without recrystallization.

The 3β-iodo-5β-androstan-17-one (2) (118.6 g, 297.0 mmol), ethylene glycol (200 ml) and p-toluene sulfonic acid (2.0 g) in benzene (2500 ml) were mixed. The mixture was refluxed under a Dean-Stark trap for 72 hours. The solution was then washed with saturated sodium bicarbonate and water, and dried over magnesium sulfate. The solvent was removed under reduced pressure and the remaining material recrystallized from ether to yield 128.7 g (98%) of 3β-iodo-5β-androstan-17-ethyleneketal.

Cuprous cyanide (20.0 g, 223.3 mmol) was placed in a dry 500 ml 3-neck round bottom flask equipped with a magnetic stirrer. The system was flushed with nitrogen and dry tetrahydrofuran (100 ml) was added to the flask. The suspension was cooled to −70° C. and methyllithium 1.5M (in diethyl ether, 290 ml, 436 mmol) was added via cannula. The solution was allowed to warm to 0° C. for 5 minutes, which resulted in a clear tan solution. After recooling to −70° C., the 3β-iodo-5β-androstan-17-ethyleneketal (24.2 g, 54.5 mmol) in 100 ml dry tetrahydrofuran was added via a syringe. The solution was then warmed to room temperature (25° C.) and stirred for 18 hours under nitrogen. The solution was extracted with 20 with 250 ml of 90% saturated $NH_4Cl$/10% conc. NHOH. The solvent was removed under reduced pressure. Recrystallization from methanol (600 ml) yielded 3β-methyl-5β-androstan-17-ethyleneketal, 14.09 g (78%).

The 3β-methyl-5β-androstan-17-ethyleneketal (11.20 g, 33.8 mmol) was dissolved in acetone (250 ml). p-Toluene sulfonic acid (200 mg) and $H_2O$ (80 ml) were added and the solution refluxed for 2 hours. The solution was evaporated, taken up in ether (80 ml), washed with saturated sodium bicarbonate, water, then dried over magnesium sulfate. The solution was filtered and evaporated to give a colorless solid which was recrystallized from methanol to yield 3β-methyl-5β-androstan-17-one as colorless plates (8.74 g, 90%). The melting point of this composition is 145°–147° C.

The compositions of the instant invention are used in combatting obesity. According to the method of the instant invention α-HET and β-HET analogs having a 3β-methyl group are provided. These compounds are then administered to mammals to control obesity in pharmaceutically acceptable and therapeutically effective amounts. The compounds may be administered orally, intraperitoneally or intravenously. Known methods of formulating the compound for administration are suitable. Tablet pressing for oral administration or sesame oil for intraperitoneal administration are adequate.

The following examples are intended to illustrate the invention but are not meant to unduly limit the invention in scope or spirit.

EXAMPLE 3

Forty C57-WH mice were maintained five per cage in a temperature-controlled room (25° C.) with 12-h light/day (7:00 A.M. to 7:00 P.M.). All mice were at ten weeks of age when the experiment was begun. Initial body weights of the mice were not significantly different (15.0±1.3 g).

The mice were divided into four groups: β-MET-treated female; control female; β-MET-treated male; and control male (for each group, n=10). All β-MET-treated animals received 0.07 mg (~4.6 mg/kg) of the β-MET administered as a suspension in sesame oil by PO intubation three times weekly. The control animals received only sesame oil. The mice were treated for a period of 14 weeks with access to Purina Laboratory chow and water ad libitum. Body weights were recorded weekly, and food consumption was determined by subtracting the food remaining from the food supplied at the beginning of each week.

Student's t-test was used in all statistical analyses of the data. Data are presented as means ±SD from the four groups of mice. Differences were considered significant at $p<0.01$.

Figure 5:
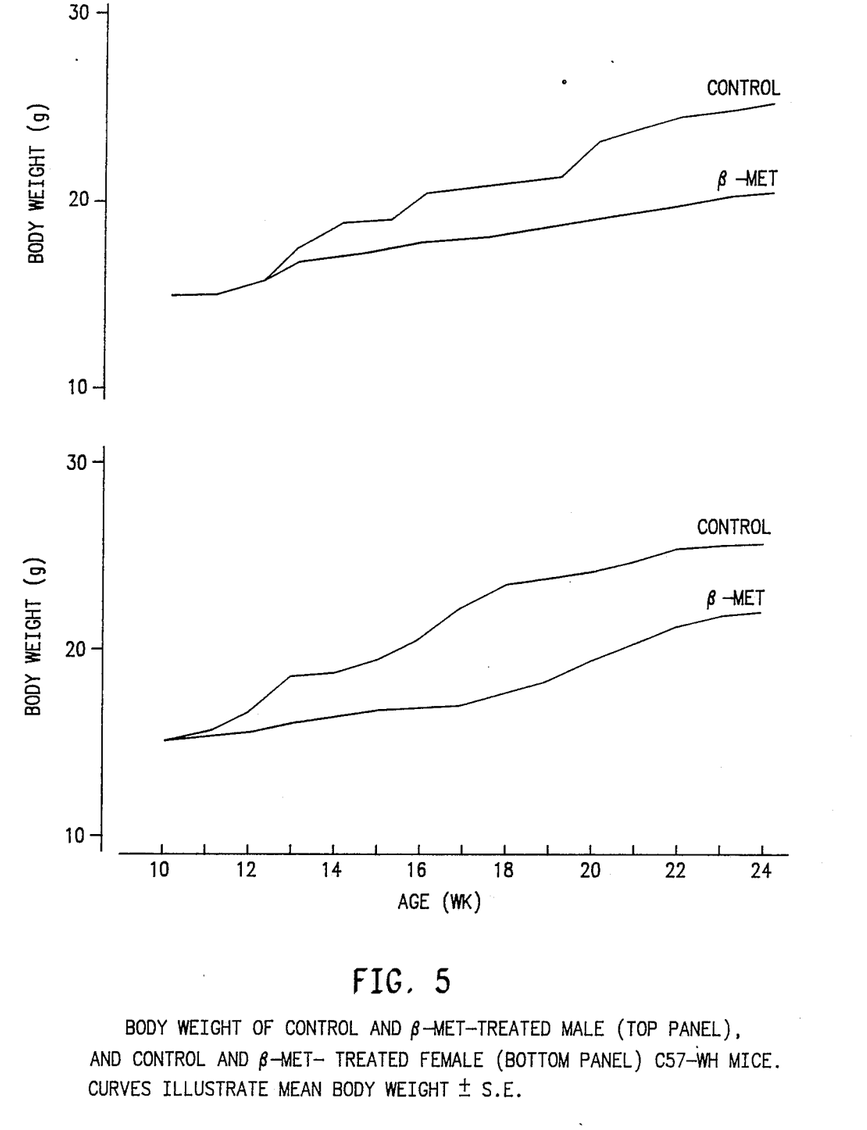
FIG. 5 is a graph depicting the changes in body weight of control and β-MET-treated C57-WH mice over a period of 14 weeks. The curves illustrate mean body weight ±SE.
Figure 6:
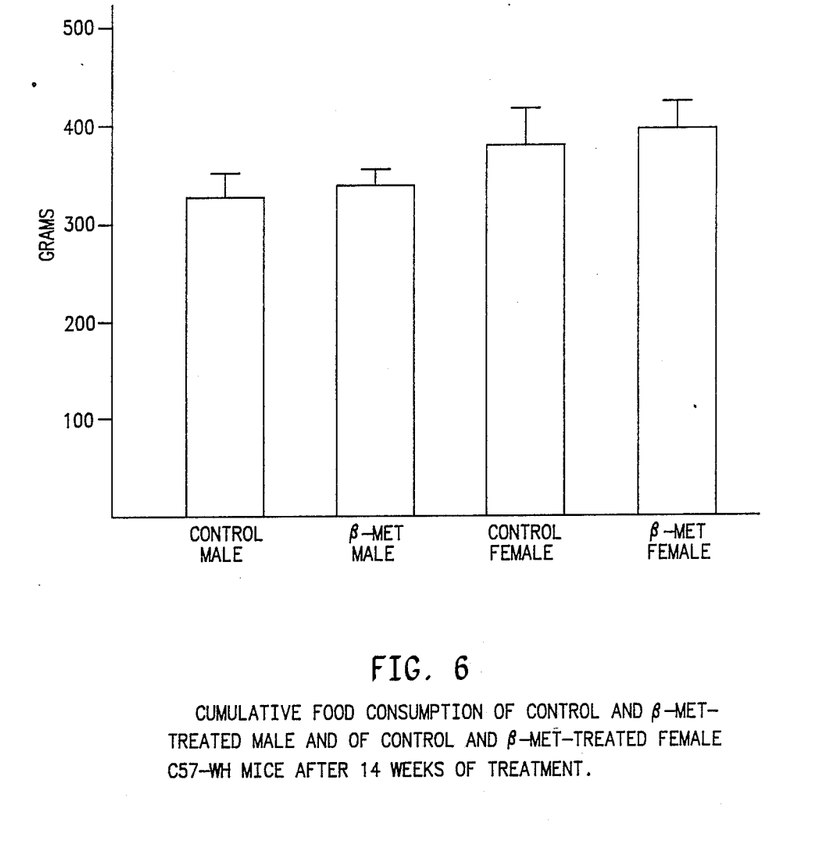
FIG. 6 is a bar graph depicting the cumulative food consumption (in grams) of control and β-MET-treated C57-WH mice over a 14 week period.

Treatment with 3β-methyl-5β-androstan-17-one significantly inhibits weight gain of both male and female C57-WH mice (FIG. 5) without suppressing appetite (FIG. 6). After 14 weeks, the mean weight of the control male mouse was 24.8 g while that of the β-MET-treated male mouse was 20.7 g. The mean weight of the control female mouse was 26.1 g while that of the β-MET-treated female mouse was 21.8 g. The differences in mean weights of the control and β-MET-treated male mice are statistically significant after the sixth week of treatment. For the female control and β-MET-treated mice, a significant difference in mean weights was observed after the third week of treatment.

Cumulative food consumption of the control and the β-MET-treated male mice were not significantly different (FIG. 6). Similarly, the food intake of the control female was not significantly different from that of the β-MET-treated female.

While the prior art teaches a variety of uses for DHEA, its use in obesity control is severely hampered by its simultaneous estrogenic side effects. The following example is provided to demonstrate the clinical impracticability of using DHEA for mammalian obesity control. It is also demonstrated that one of the compounds of the instant invention β-MET does not exhibit similar estrogenic activity.

EXAMPLE 4

DHEA Estrogenic Effects

Immature female C57-WH mice were maintained at 25° C. at 12 hours light/12 hours dark (lights on at 0800 h and off at 2000 h). Purina Lab Chow and water were available ad libitum. The control and each experimental group of animals consisted of six mice. Treatment began after an acclimation period of five days. Beginning at 27 days of age and continuing for three consecutive days, the mice were orally intubated with DHEA or β-MET suspended in sesame oil. The control mice received only sesame oil. Between 1400–1600 h on day 30, all animals were sacrificed by an overdose of ether. Uteri were removed, cleaned of adventitious tissue, and weighed to the nearest 0.5 mg.

All reported results are expressed as the mean plus or minus the standard error (mean±SE).

TABLE 1

Effect of dehydroepiandrosterone (DHEA) and β-MET on uterine weight of the immature mouse. DHEA and β-MET were administered for three consecutive days, beginning on day 27. Animals were sacrificed on day 30.

| Daily dose of β-MET (mg/kg body weight) | Uterine weight (mg/100 g body weight) |
|---|---|
| control | 58.0 ± 3 |
| 400.0 (DHEA) | 257.0 ± 5 |
| 100.0 | 60.0 ± 2 |
| 400.0 | 64.3 ± 6 |

EXAMPLE 5

In humans, oral administration is preferred. The substance may be pressed into tablet form with conventional binders or it may be suspended in a vegetable oil and taken in capsule form. Lipid solubility of the substance affords good absorption across the mucosal barrier.

The effective human dose of the substance is approximately 10 mg/kg body weight/day, and this may be in single or divided administrations.

EXAMPLE 6

β-MET was tested for mutagenicity by administration to a his⁻auxotrophic mutant of *Salmonella typhimurium*. β-MET was administered alone and with a liver homogenate fraction from a rat that had been treated with polychlorinated biphenyl. The results indicate that β-MET is not mutagenic.

The LD$_{50}$ of β-MET administered orally in mice could not be accurately determined. However, five male and five female C57-WH mice, each weighing approximately 15 g, received 200 mg of β-MET, suspended in sesame oil, by p.o. intubation. All of the animals survived. These results suggest that the LD$_{50}$ (oral) in mice is >10,000 mg/kg.

Moreover, short-term treatment with relatively large doses of β-MET (approximately 20x the effective antiobesity dose in mice) appears not to be harmful to mice. Five male and five female C57-WH mice (age: ~11 weeks, weight: ~15 g each) each received 200 mg/kg of β-MET, suspended in sesame oil, by p.o. intubation every second day for a period of thirty days. Another group of ten matched controls received only the sesame oil. At the end of the thirty day period, all experimental mice were alive and apparently healthy, exhibiting no obvious behavioral or external physical differences from controls. Abnormalities such as hypertrophic lymph nodes, diarrhea, bloody stools, or loss of hair luster were not seen. Examination of visible membranes including nasal cavities and conjunctiva yielded no abnormal findings. Postmortem studies of the experimental mice revealed no gross abnormalities or visible pathological changes.

I claim:

1. A steroid selected from the group consisting of metabolically stable, pharmaceutically acceptable and therapeutically effective analogs of 5-β-androstan-3-α-ol-17-one having the structure:

wherein R$_1$ is selected from the group consisting of Cl, F, and Br.

2. A steroid selected from the group consisting of metabolically stable, pharmaceutically acceptable and therapeutically effective analogs of 5-β-androstan-3-β-ol-17-one having the structure:

wherein R$_1$ is selected from the group consisting of H, Cl, F and Br.

3. 3-α-methyl-5-β-androstan-17-one.
4. 3-β-methyl-5-β-androstan-17-one.
5. A method of weight reduction in mammals comprising the steps of providing and administering a therapeutically effective dosage of the steroid of claim 1 to said mammals in such quantity, for such time and under such conditions to induce weightloss in said mammals.
6. A method of weight reduction in mammals comprising the steps of providing and administering a therapeutically effective dosage of the steroid of claim 2 to said mammals in such quantity, for such time and under such conditions to induce weightloss in said mammals.
7. A method of weight control in mammals comprising the steps of providing and administering a therapeutically effective dosage of the steroi of claim 3 to said mammals in such quantity, for such time and under such conditions to induce weightloss in said animals.
8. A method of weight control in mammals comprising the steps of providing and administering a therapeutically effective dosage of the steroid of claim 4 to said mammals in such quantity, for such time and under such conditions to induce weightloss in said animals.
9. The method of claim 5 wherein the compound is administered intraperitoneally.
10. The method of claim 6 wherein the compound is administered intraperitoneally.
11. The method of claim 7 wherein the compound is administered intraperitoneally.
12. The method of claim 8 wherein the compound is administered intraperitoneally.
13. The method of claim 5 wherein the compound is administered intravenously.
14. The method of claim 6 wherein the compound is administered intravenously.
15. The method of claim 7 wherein the compound is administered intravenously.
16. The method of claim 8 wherein the compound is administered intravenously.
17. The method of claim 5 wherein the compound is administered orally.
18. The method of claim 6 wherein the compound is administered orally.
19. The method of claim 7 wherein the compound is administered orally.
20. The method of claim 8 wherein the compound is administered orally.

* * * * *

UNITED STATES PATENT AND TRADEMARK OFFICE
CERTIFICATE OF CORRECTION

PATENT NO. : 4,897,390

DATED : January 30, 1990

INVENTOR(S) : RODNEY C. RUHE

It is certified that error appears in the above-identified patent and that said Letters Patent is hereby corrected as shown below:

Column 7, line 25, delete "NHOH" after "conc." and substitute --$NH_4OH$--;

Column 7, line 31, delete "$H_{20}$" after "and" and substitute -- $H_2O$ --;

Column 8, lines 4, 44, "ad libitum" should be italicized both occurrences; and

Column 9, line 16, "his" should be italicized.

UNITED STATES PATENT AND TRADEMARK OFFICE
CERTIFICATE OF CORRECTION

PATENT NO. : 4,897,390

DATED : January 30, 1990

INVENTOR(S) : RODNEY C. RUHE

It is certified that error appears in the above-identified patent and that said Letters Patent is hereby corrected as shown below:

Column 9, lines 53-61 (claim 1), the structure should read as follows:

Column 9, line 63, insert --H,-- after "of";

Column 10, line 32, delete "steroi" after "the" and substitute --steroid--;

Signed and Sealed this

Seventh Day of January, 1992

Attest:

HARRY F. MANBECK, JR.

Attesting Officer

Commissioner of Patents and Trademarks